(12) United States Patent
Wu et al.

(10) Patent No.: US 7,086,780 B2
(45) Date of Patent: Aug. 8, 2006

(54) METHODS FOR SPECTRALLY CALIBRATING CT IMAGING APPARATUS DETECTORS

(75) Inventors: Xiaoye Wu, Rexford, NY (US); Neil Barry Bromberg, Milwaukee, WI (US); Alexander Kolker, Milwaukee, WI (US); Piero Ugo Simoni, Greenfield, WI (US); Thomas Louis Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 145 days.

(21) Appl. No.: 10/850,009

(22) Filed: May 20, 2004

(65) Prior Publication Data

US 2005/0259784 A1 Nov. 24, 2005

(51) Int. Cl.
*G01D 18/00* (2006.01)
(52) U.S. Cl. .............................. 378/207; 378/5; 378/18; 378/19; 250/363.09
(58) Field of Classification Search .................... 378/4, 378/5, 19, 207, 901, 18; 250/363.09
See application file for complete search history.

(56) References Cited

U.S. PATENT DOCUMENTS

| 5,450,462 | A | 9/1995 | Toth et al. |
| 5,579,359 | A | 11/1996 | Toth |
| 6,115,487 | A | 9/2000 | Toth et al. |
| 6,266,434 | B1 | 7/2001 | Toth et al. |
| 6,325,539 | B1 | 12/2001 | Bromberg et al. |
| 6,327,329 | B1 | 12/2001 | Bromberg et al. |
| 2004/0022364 | A1* | 2/2004 | Stierstorfer et al. ........ 378/207 |
| 2004/0179646 | A1* | 9/2004 | Li et al. ....................... 378/19 |
| 2004/0218728 | A1* | 11/2004 | Heismann .................... 378/207 |

FOREIGN PATENT DOCUMENTS

| EP | 0981997 A1 | 3/2000 |
| EP | 1355321 A2 | 10/2003 |
| EP | 1389444 A1 | 2/2004 |

* cited by examiner

*Primary Examiner*—Edward J. Glick
*Assistant Examiner*—Anastasia Midkiff
(74) *Attorney, Agent, or Firm*—Carl B. Horton, Esq.; Armstrong Teasdale LLP

(57) ABSTRACT

A method for calibrating a computed tomographic imaging apparatus having a gantry, a radiation source operable at a plurality of kVp's, and a detector array having a plurality of detector elements includes using a system detection function to estimate signals of each detector element that would have been detected through air and through a given thickness of water to determine estimated datasets. The estimated datasets are used to determine data pair sets each comprising a normalized water projection value and an ideal projection value for each detector element. The method further includes determining and storing a representation of a mapping function of the normalized water projections values to the ideal projection values in a memory of the computed tomographic imaging apparatus as a spectral calibration of the computed tomographic imaging apparatus.

20 Claims, 2 Drawing Sheets

METHODS FOR SPECTRALLY CALIBRATING CT IMAGING APPARATUS DETECTORS

BACKGROUND OF THE INVENTION

This invention relates generally to methods for computed tomography (CT) imaging and more particularly to methods and apparatus for calibrating CT imaging apparatus detectors to produce images having reduced artifacts.

X-ray CT measures x-ray attenuation through an object with a plurality of detector elements at various angular positions with respect to the object. With appropriate data processing, a cross-sectional image revealing inner structures of the object can be reconstructed. Reconstructed images represent a property of an object in response to x-rays (or other radiation), namely, the x-ray (or other radiation) linear attenuation. To reconstruct artifact free images, calibration of an CT imaging system and an appropriate correction must to be applied in the reconstruction process. For example, calibration and correction related detector response to incident x-ray spectrum must be performed. X-ray spectra often have wide energy bandwidths, typically from a few tens of keV to more than a hundred keV. In third generation CT configurations an X-ray tube and detectors rotate together around an object. This configuration makes image quality sensitive to spectral characteristics of detector elements. This sensitivity tends to be greatest for detector elements near iso-center, the axis around which the CT gantry rotates. Thus, effort has to be expended to produce and select detector elements with nearly identical spectral characteristics.

After detector elements are arranged in a detector array, a spectral calibration can be performed to determine residual spectral response differences among detector elements and to ensure that reconstructed images of water phantoms are uniform and free of artifacts. Inaccurate determination of spectral response differences between detector elements results in rings and bands in images around the iso-center. In at least one known method for spectral calibration, uniform phantoms made of water-like material are used for calibration. By scanning these phantoms, the detector response to an x-ray spectrum attenuated through a given length of water can be determined. However, multiple phantoms of various sizes are often required to cover the attenuation range needed for some types of imaging, including medical imaging, leading to lengthy calibration times. Spectral calibration is often performed every few months. Because of the complexity of the calibration procedure, well-trained technicians must usually be employed to perform these calibrations.

BRIEF DESCRIPTION OF THE INVENTION

In one aspect, some configurations of the present invention provide a method for calibrating a computed tomographic imaging apparatus having a gantry, a radiation source operable at a plurality of kVp's, and a detector array having a plurality of detector elements. The method includes using a system detection function to estimate signals of each detector element that would have been detected through air and through a given thickness of water to determine estimated datasets. The estimated datasets are used to determine data pair sets each comprising a normalized water projection value and an ideal projection value for each detector element. The method further includes determining and storing a representation of a mapping function of the normalized water projections values to the ideal projection values in a memory of the computed tomographic imaging apparatus as a spectral calibration of the computed tomographic imaging apparatus.

In another aspect, some configurations of the present invention provide a computed tomographic imaging apparatus having a gantry, a radiation source operable at a plurality of kVp's, and a detector array having a plurality of detector elements. The apparatus is configured to use a system detection function to estimate signals of each detector element that would have been detected through air and through a given thickness of water to determine estimated datasets. The apparatus is configured to utilize the estimated datasets to determine data pair sets each comprising a normalized water projection value and an ideal projection value for each detector element. Also, the apparatus is configured to determine and store a representation of a mapping function of the normalized water projections values to the ideal projection values in a memory as a spectral calibration.

In another aspect, some configurations of the present invention provide a computed tomographic imaging apparatus having a rotating gantry, a radiation source operable at a plurality of kVp's, and a detector array having a plurality of detector elements. The radiation source and detector array are mounted on the rotating gantry and configured to rotate with the gantry. The CT imaging apparatus is configured to determine a set of system detection coefficients utilizing air scan measurements at a plurality of kVp's of the radiation source. Utilizing the determined set of system detection coefficients, the CT imaging apparatus is also configured to determine detected signals of each detector element through air and through a given thickness of water. Using the determined detected signals, the CT imaging apparatus is also configured to determine a plurality of data pair sets having a predicted signal and an ideal signal for each detector element and to obtain a spectral correction for the detector elements using the determined data pair sets.

Configurations of the present invention in principle do not require the scanning of phantoms. Instead, some configurations of the present invention are able to determine x-ray detection efficiency as a function of photon energy for individual detector elements by measuring x-ray projections through air at multiple kVps. With the detection efficiencies thus determined, spectral errors for an x-ray spectrum attenuated through any given size of water-like object can also be determined. Configurations of the present invention thus can be performed in the time required for conventional air calibrations and can be fully automated, making daily spectral calibration feasible. Moreover, some configurations of the present invention enable spectral calibration of arbitrary or dynamically varying beam filters (such as bow tie filters) that can be used to reduce radiation dose to the patient, even through physical calibration is not necessarily performed with a shape of a particular beam filter.

DETAILED DESCRIPTION OF THE INVENTION

Figure 1:
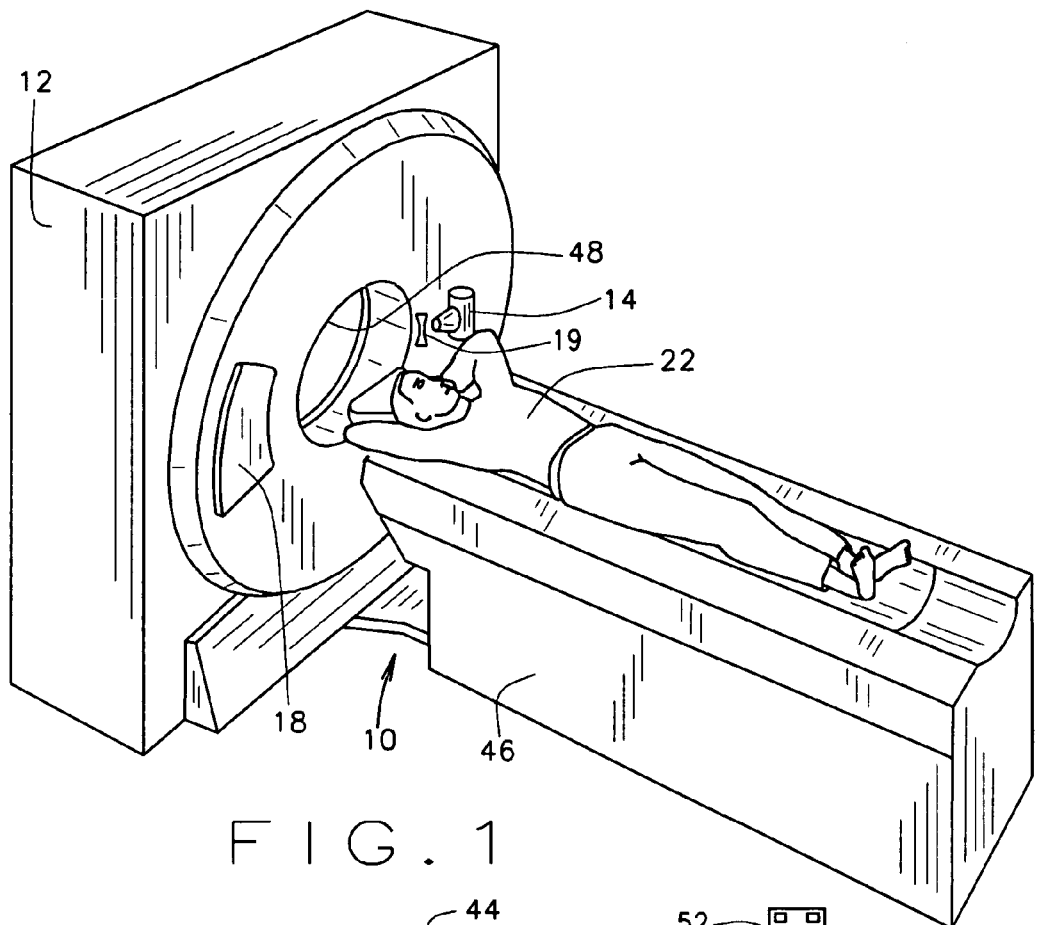
FIG. 1 is a pictorial drawing representative of some configurations of CT imaging apparatus of the present invention.

Example embodiments of methods and apparatus that facilitate calibration of CT imaging apparatus and CT imaging methods and apparatus having reduced image artifacts are described below in detail. A technical effect of the methods and apparatus described herein include at least one of calibration of CT imaging apparatus, reduction of image artifacts, and the determination of detector element detection efficiency as a function of photon energy for individual detector elements.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
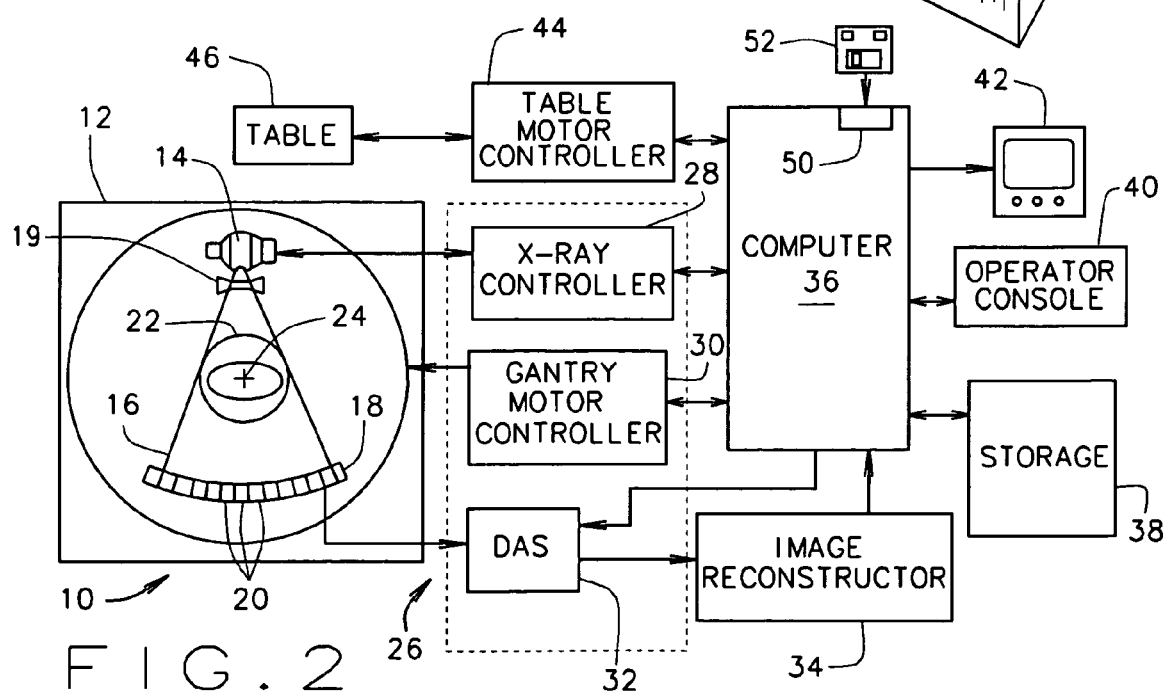
FIG. 2 is a functional block diagram representative of the CT imaging apparatus of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. A filter, for example, a bowtie beam filter 19, may be provided. If provided, the bowtie beam filter may be operated either statically or dynamically. Detector array 18 is formed by a plurality of detector rows (not shown) including a plurality of detector elements 20 which together sense the projected x-rays that pass through an object 22, such as a medical patient between array 18 and source 14. For calibration purposes, a phantom (for example, a water-based phantom) is used as object 22. Each detector element 20 produces an electrical signal that represents the intensity of an impinging x-ray beam and hence can be used to estimate the attenuation of the beam as it passes through object 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 (or a suitable display of another type) allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position object 22 in gantry 12. Particularly, table 46 moves portions of object 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Thus, a rotating gantry is not present in all configurations of the present invention. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In many of the example embodiments described herein, it is assumed that an x-ray source 14 is used and that radiation beam 16 is an x-ray beam. However, with the use of suitable detector elements 20, a different type of radiation source 14 can be substituted for x-ray source 14. In such configurations, beam 16 can more generally be referred to as a radiation beam 16.

Spectral errors that appear in reconstructed CT images, particularly third generation CT images, result from uncontrolled filtration of radiation beam 16 (for example, shadowing of an antiscatter collimator) and differences in signal production efficiency between detector elements as a function of incident photon energy. Thus, an incident x-ray spectrum attenuated by the same thickness of water will result in unequal signals being produced from different detector elements 20. Because attenuation of x-rays 16 through water is strongly dependent upon photon energy, and detection efficiency is also a function of photon energy, a difference in detected signal can not be compensated using air measurements. Thus, rings and bands occur in third generation CT images.

A detector array 18 in many configurations comprises a plurality of detector modules, i.e., groups of detector elements 20 that comprise a single unit out of a plurality of such units forming a portion of detector array 18. As the number of detector 18 rows in a CT imaging system 10 increases and the number of operation modes dramatically increases, the probability of finding high quality detector modules in all detector array 18 rows decreases and staging time for phantom-based spectral calibration increases. Configurations of the present invention thus provide methods and apparatus for rapid, high sensitivity spectral calibration. Detection efficiency is used to determine spectral errors rather than phantom-by-phantom direct spectral error measurements.

In some configurations of the present invention, for a selected beam filter, a number of scans are performed at various kVp settings of x-ray tube 14. Detection efficiency for each detector element 20 is determined using changes in detected signal from these scans. Spectral errors for various path lengths of water absorber (i.e., a water-based phantom used as object 22) are determined using knowledge of the initial x-ray spectrum, the materials of a beam filter (not shown in the Figures), and detector element 20 detection efficiencies as a function of photon energy.

Some configurations of the present invention thus determine detector element 20 detection efficiencies as a function of photon energy. Spectral errors originate from several aspects, namely, beam-hardening by water, the uncontrolled beam filter, and usually most importantly, differential efficiency among the plurality of detector elements 20. Beam hardening by water is a physical property that can be calculated precisely. If the incident x-ray spectra are well-controlled, the beam hardening effect can be accurately predicted and removed. Spectral errors resulting from the uncontrolled beam filter and differential efficiency among detector elements 20 are produced by imperfections in manufacturing and are thus unpredictable. The combined effect of uncontrolled beam filter and differential efficiency can be combined mathematically into a deviation in detection efficiency. Various configurations of the present invention determine the detection efficiency as a function of incident photon energy by comparing relative signal level among several x-ray spectra.

Figure 3:
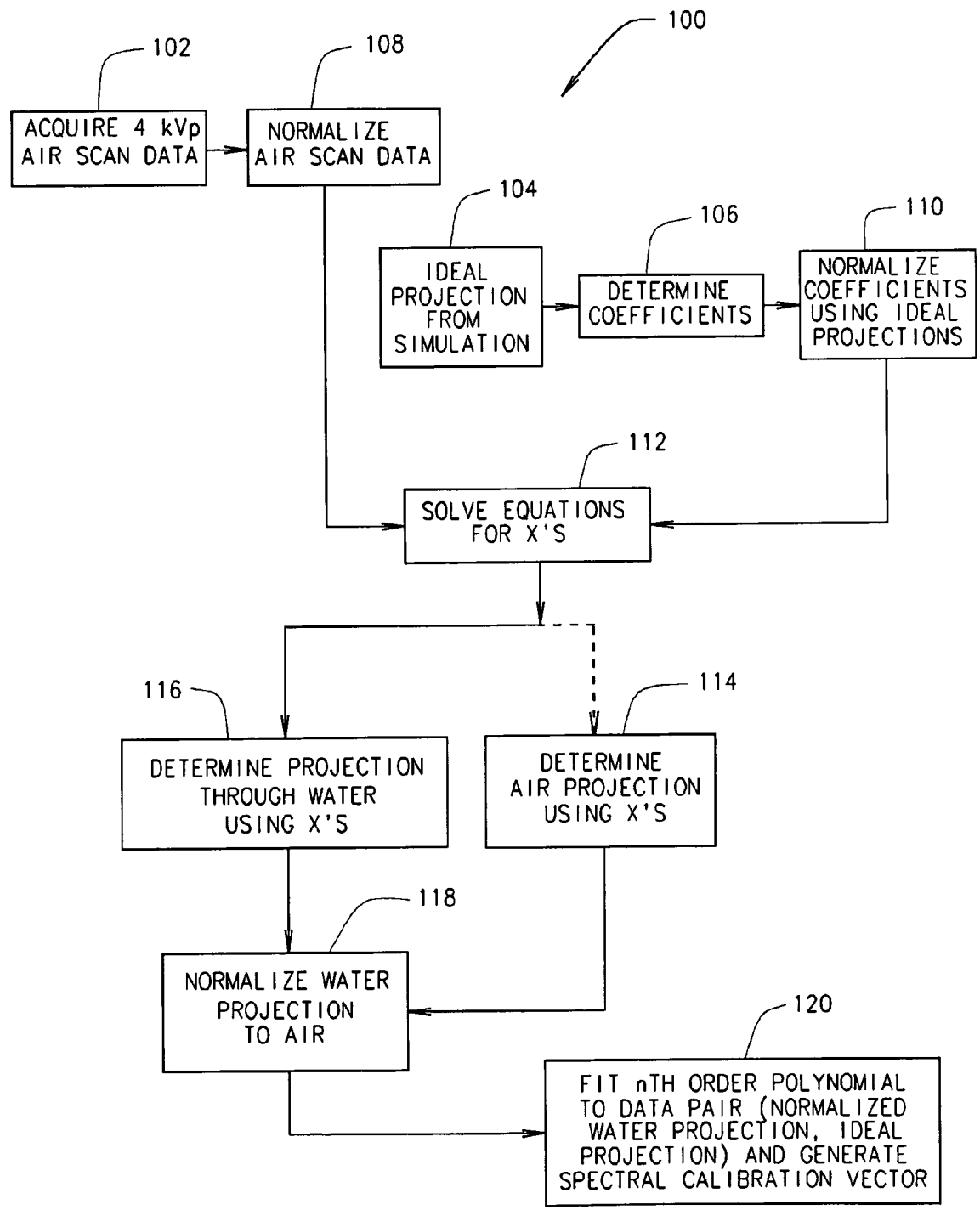
FIG. 3 is a flow chart representative of various configurations of calibration procedures of the present invention.

FIG. 3 is a flowchart 100 illustrating example processes utilized by CT imaging system 10. Many of the steps shown in flowchart 100 can be performed automatically under control of computer 36 under suitable program control (e.g., a firmware program built into computer 36 or provided device 50). However, it is not required that the steps be performed in an automatic progression. The technical effect of methods and apparatus utilizing processes represented by flowchart 100 is achieved by a user first operating CT imaging system to acquire (i.e., measure) a detected signal dataset {D(i, kv)} at 102, where i is the detector element 20 index, for each kVp setting provided by the CT system, and without any object in the path of x-ray beam 16 except for system beam filter 19, if present. In some configurations, there are four kVp settings, so four scans are recorded at 102. In other configurations, a greater or lesser number of scans are recorded. Separately, at 104, ideal projections are simulated. More particularly, in some configurations, the following parameters are defined in the simulation:

S(E, kv) is a spectrum as a function of x-ray kv (kilovolts) and photon energy E;

b(E, kv, i) is a combined material attenuation of the beam filters for detector i (this function can change with time for a dynamically varying beam filter, and in such cases, is also a function of t);

$\mu$(A, E) is a linear attenuation coefficients of a material A;

$X_n(i)$ are a set of unknown coefficients to be solved;

$T_L$ is the scintillator thickness of the detector elements.

An ideal projection value $P_{ideal}(i, kv)$ is written:

$$P_{ideal}(i, kv) = \Sigma_E \{S(E, kv) * E * [1-\exp(-\mu(\text{scintillator}, E) * T_L)] * \exp(-b(E, kv, i))\} \quad (1)$$

The predicted (i.e., estimated) projection values (i.e., ideal projection coefficients) form a dataset {P(i, kv)} that takes into account physical properties of detection components of imaging system 10. The dataset of ideal projection coefficients is determined at 106 from the simulation at 104. (The "detection components of imaging system 10" include detector elements 20, radiation source 14, and filter 19, if present, and other spectral effects introduced by detector array 18.) The predicted projection values are written:

$$P(i, kv) = \Sigma_E\{S(E, kv)*E*[1-\exp(-\mu(\text{scintillator}, E)*T_L)]*\exp(-b(E, kv, i)*f(E, i))\} \quad (2)$$

where $f(E, i)$ is the system detection function for photons with energy E. The system detection function $f(E, i)$ can be modeled as a smooth function of E, for example and not by way of limitation, a polynomial with system detection coefficients $X_n(i)$ such as $f(E, i) = X_0(i) + X_1(i)*E + X_2(i)*E^2 + X_3(i)*E^3$.

The acquired dataset $\{D(i, kv)\}$ (subtracting an electronic offset reading) is normalized at 108, using an expression written $D_{norm}(i, kv) = D(i, kv)/\Sigma_i D(i, kv)$, where $D_{norm}(i, kv)$ represents the normalized measured data.

The ideal projection data coefficients are normalized at 110, using an expression written $P_{norm}(i, kv) = P(i, kv)/\Sigma_i P_{ideal}(i, kv)$.

In various configurations of the present invention, the various values of system detection coefficients $X_n(i)$ are determined at 112 for each detector element using a relationship written $P_{norm}(i, kv) = D_{norm}(i, kv)$ by solving a set of linear equations, if system detection function $f(E, i)$ is expressed in a polynomial form as shown herein. Otherwise, if necessary, nonlinear or numerically-derived techniques can be used to determine the system detection function $f(E, i)$.

In some configurations, an air projection dataset $\{A(i, kv)\}$ is estimated at 114 using the values of $X_n(i)$. The model $A(i, kv)$ is written:

$$A(i, kv) = \Sigma_E\{S(E, kv)*E*[1-\exp(-\mu(\text{scintillator}, E)*T_L)]*\exp(-b(E, kv, i)*f(E, i))\}.$$

Also, at 116, a projection dataset through water $\{W(i, kv, L)\}$ for path length L is estimated at 116 using the values of $X_n(i)$:

$$W(i, kv, L) = \Sigma_E\{S(E, kv)*E*[1-\exp(-\mu(\text{scintillator}, E)*T_L)]*\exp(-b(E, kv, i)*f(E, i))*\exp(-\mu(\text{water}, E)*L)\}.$$

Next, the water projection is logarithmically normalized to the air projection at 118 to produce a projection value Proj(i, kv, L) written:

$$\text{Proj}(i, kv, L) = -\log[W(i, kv, L)/A(i, kv)].$$

An nth order polynomial is fitted to the data pair (normalized water projection, ideal projection) = (Proj(i, kv, L), Ideal(i, kv, L)) to generate the spectral calibration vector at 120. The normalized water projection data Proj(i, kv, L) is mapped to the ideal projection value, which is written as:

$$\text{Ideal}(i, kv, L) = \mu*L,$$

where $\mu$ is a constant that is equal to the water linear attenuation at the average x-ray energy for a given kVp, and spectral cal vectors are also generated. The purpose of spectral cal for water is to linearize a measured projection value to water path length. More particularly, a mapping function Proj(i, kv, L) => Ideal(i, kv, L) is the spectral calibration, which can either be in the form of a look-up table or in some functional form. A polynomial fit can characterize the mapping. The coefficients of the mapping polynomial can be obtained by fitting data pairs (Proj(i, kv, L), Ideal(i, kv, L)) generated at various water path length L.

Steps 114, 116, 118, and 120 can be iterated with different bowtie filter 19 shapes, if bowtie filter 19 (or another adjustable filter) is present to obtain different mappings for different values of b(E, kv, i). The different mappings are especially useful for applying a spectral correction to adaptive or dynamic beam filters that change the beam filter shape before or during patient scanning.

Thus, an ideal spectral effect is modeled by simulation of an x-ray beam spectrum and its interaction with materials such as filters in the beam path and water phantoms. Deviation from the ideal model is determined from the measurements at multiple kVp's. Detector detection efficiency as a function of photon energy and any additional filtration in the beam path is modeled as the absorption coefficients of a polynomial function directly as shown herein, or two distinct materials plus a polynomial, or any other smooth functional form. System detection coefficients $X_n(i)$ are determined from measurements of air scans through known beam filters or through air scans without beam filters, at a plurality of kVp's. The number of kVp's required in some configurations is equal to or greater than the number of unknown coefficients in the functional form, or, in some other configurations, a least squares method of obtaining coefficients is used. The functional form can be further reduced to linear terms of the unknown coefficients, simplifying the process of obtaining the solutions of the unknown coefficients. Upon obtaining the coefficients in the functional form, the detected signal of each detector element through the beam filter and through a given thickness of water is determined for a spectrum at a given kVp. The spectral errors of any detector element can be determined by comparing the calculated signal, normalized to a calculated air signal, with the negative of the logarithm taken and incorporating the detection functional form, to the ideal signal (or a corrected signal). The ideal signal used here is a linear function of the water penetration length. By making such determinations for all penetration lengths of water relevant to imaging (for example, in a medical imaging application), a data pair set of predicated signal and ideal signal is built for each detector element. This data pair set provides a direct spectral correction for removing beam hardening in water and eliminating detector errors. This data pair set can be fitted by a polynomial, providing fast spectral correction. Moreover, the spectral correction can be performed dynamically or statically for any beam filter shape, upon the determination of the system detection coefficients $X_n(i)$. For example and without limitation, a spectral correction can be applied to adaptive beam filters that change the beam filter shape before or during patient scanning for radiation dose reduction.

Configurations of the present invention can be used in combination with other calibration methods. For example, spectral calibration using phantoms can be used in combination with configurations of the present invention to achieve improved image quality by accounting for non-spectral related detector efficiency deviation such as x-ray scatter.

Configurations of the present invention described herein are directed to spectral correction for water or water-like materials. However, configurations of the present invention that determine detection efficiency as a function of photon energy for detector elements can also be used in other applications. Such other applications include, but are not limited to, correction of image artifacts originated from spectral changes due to materials other than water or water-like materials, such as bones, contract agents, metal implants, or other materials. Correction factors can be obtained in a manner similar to that described above by including the extra materials in the processing.

It will thus be appreciated that configurations of the present invention provide accurate determination of the spectral errors for individual detector elements across an entire field of view. These spectral errors can be characterized as a high-order polynomial for fast data correction. Besides providing high accuracy, configurations of the present invention do not require calibration phantoms, thereby allowing rapid and simple calibration. The process can be fully automated and performed daily. Configurations of the present invention make possible spectral calibration for adaptive beam filters that reduce radiation dose to the patient. Such an adaptive beam filter can dynamically change filter shape according to patient size, making it difficult and time-consuming to perform spectral calibration on each of the beam filter configurations. However, configurations of the present invention determine detector response to x-rays captured under a given filter, or no beam filter at all, so that the spectral correction for any given beam filter can be dynamically calculated based on the knowledge of the material in the beam filter, and the determination of $X_n(i)$.

While the invention has been described in terms of various specific embodiments, those skilled in the art will recognize that the invention can be practiced with modification within the spirit and scope of the claims.

What is claimed is:

1. A method for calibrating a computed tomographic imaging apparatus comprising a gantry, a radiation source operable at a plurality of kVp's, and a detector array comprising a plurality of detector elements, said method comprising:
    acquiring a measured dataset utilizing air scan measurements at a plurality of kVp's of the radiation source;
    using a system detection function to estimate signals of each detector element that would have been detected through air and through a given thickness of water to determine estimated datasets;
    utilizing the estimated datasets to determine data pair sets each comprising a normalized water projection value and an ideal projection value for each detector element; and
    determining and storing a representation of a mapping function of the normalized water projections values to the ideal projection values in a memory of the computed tomographic imaging apparatus as a spectral calibration of the computed tomographic imaging apparatus.

2. A method in accordance with claim 1 wherein the radiation source and detector array are mounted on a rotating gantry, and said acquiring a measured dataset comprises rotating the radiation source and the detector array about a center of rotation.

3. A method in accordance with claim 1 wherein the system detection function is a polynomial having system detection coefficients.

4. A method in accordance with claim 1 wherein storing the representation of the mapping function comprises storing coefficients of a mapping polynomial.

5. A method in accordance with claim 1 wherein said utilizing the estimated datasets comprises normalizing an estimated projection dataset through water to a estimated projection dataset through air.

6. A method in accordance with claim 5 wherein said normalizing an estimated projection dataset through water to a estimated projection dataset through air comprises a logarithmic normalization.

7. A method in accordance with claim 1 further comprising:
    simulating ideal projections to obtain an ideal projection dataset comprising ideal projection values; and
    using the ideal projection dataset and the measured dataset to determine the system detection function;
    and wherein said determining the data pair sets further utilizes said ideal projection dataset.

8. A method in accordance with claim 7 wherein the radiation source is an x-ray source and determining a system detection function utilizing air scan measurements at a plurality of kVp's comprises operating the x-ray source at a plurality of kVp's.

9. A method in accordance with claim 7 wherein said acquiring the measured dataset further comprises normalizing acquired measurements.

10. A method in accordance with claim 7 wherein the computed tomographic imaging apparatus comprises an adjustable filter and said estimated datasets are determined for a plurality of shapes of the adjustable filter; and further comprising iterating said determining data pair sets and said determining and storing a representation of a mapping function of the normalized water projections to ideal signal values for each said shape of said plurality of shapes of the adjustable filter.

11. A computed tomographic imaging apparatus comprising a gantry, a radiation source operable at a plurality of kVp's, and a detector array comprising a plurality of detector elements, said apparatus configured to:
    acquire a measured dataset utilizing air scan measurements at a plurality of kVp's of the radiation source;
    use a system detection function to estimate signals of each detector element that would have been detected through air and through a given thickness of water to determine estimated datasets;
    utilize the estimated datasets to determine data pair sets each comprising a normalized water projection value and an ideal projection value for each detector element; and
    determine and store a representation of a mapping function of the normalized water projections values to the ideal projection values in a memory of the computed tomographic imaging apparatus as a spectral calibration of the computed tomographic imaging apparatus.

12. An apparatus in accordance with claim 11 wherein the radiation source and detector array are mounted on a rotating gantry, and to acquire a measured dataset, said apparatus is configured to rotate the radiation source and the detector array about a center of rotation.

13. An apparatus in accordance with claim 11 wherein the system detection function is a polynomial having system detection coefficients.

14. An apparatus in accordance with claim 11 wherein to store the representation of the mapping function, said apparatus is configured to store coefficients of a mapping polynomial.

15. An apparatus in accordance with claim 11 wherein to utilize the estimated datasets, said apparatus is configured to normalize an estimated projection dataset through water to a estimated projection dataset through air.

16. An apparatus in accordance with claim 15 wherein to normalize an estimated projection dataset through water to a estimated projection dataset through air, said apparatus is configured to perform a logarithmic normalization.

17. An apparatus in accordance with claim 11 further configured to:
    simulate ideal projections to obtain an ideal projection dataset comprising ideal projection values; and
    use the ideal projection dataset and the measured dataset to determine the system detection function;
    and wherein said apparatus is further configured to utilize the ideal projection dataset to determine the data pair sets.

18. An apparatus in accordance with claim 17 wherein the radiation source is an x-ray source and said apparatus is configured to operate the x-ray source at a plurality of kVp's.

19. An apparatus in accordance with claim 17 wherein said apparatus is further configured to normalize the measured dataset.

20. An apparatus in accordance with claim 17 further comprising an adjustable filter, and wherein said apparatus is configured to determine said estimated datasets for a plurality of shapes of the adjustable filter; and wherein said apparatus is further configured to iterate said determination of data pair sets and said determination and storing of a representation of a mapping function of the normalized water projections to ideal signal values for each said shape of said plurality of shapes of the adjustable filter.

* * * * *